United States Patent [19]

Dimo et al.

[11] Patent Number: 4,474,747

[45] Date of Patent: Oct. 2, 1984

[54] PROCESS FOR INCREASING THE TOLERANCE OF X-RAY CONTRAST MEDIA, AND CONTRAST MEDIA OBTAINED THEREBY

[75] Inventors: Ioana Dimo, Saint Mande; Bruno Bonnemain, Mitry Mory; Jean C. Hardouin, Fontenay Sous Bois; Jean Lautrou, Saint Mande, all of France

[73] Assignee: Guerbet S.A., Aulnay-Sous-Bois, France

[21] Appl. No.: 409,291

[22] Filed: Aug. 18, 1982

[30] Foreign Application Priority Data

Aug. 28, 1981 [FR] France .................................. 81 16478

[51] Int. Cl.$^3$ .............................................. A61K 49/04
[52] U.S. Cl. .................................................... 424/5
[58] Field of Search ............................................ 424/5

[56] References Cited

U.S. PATENT DOCUMENTS

| | | | |
|---|---|---|---|
| 1,870,203 | 8/1932 | Rath | 424/5 |
| 2,524,827 | 10/1950 | Papa et al. | 424/5 |
| 2,580,459 | 1/1952 | Papa et al. | 424/5 |
| 2,711,424 | 6/1955 | Suter et al. | 424/5 |
| 2,813,118 | 11/1957 | Galler | 424/5 |
| 2,890,244 | 6/1959 | Storbeck | 424/5 |
| 3,009,952 | 11/1961 | Larsen | 424/5 |
| 3,076,024 | 1/1963 | Larsen | 424/5 |
| 3,290,366 | 12/1966 | Hoey | 424/5 |
| 4,014,986 | 3/1977 | Tilly et al. | 424/5 |
| 4,073,879 | 2/1978 | Long | 424/5 |

*Primary Examiner*—Frederick E. Waddell
*Attorney, Agent, or Firm*—Young & Thompson

[57] ABSTRACT

X-ray contrast media, for which the human body has a greater tolerance than that of contrast media comprising solely iodobenzene compounds, and an opacity of the same order of magnitude as the latter contrast media, comprise mixtures of benzene compounds nuclearly substituted with a plurality of iodine atoms and of benzene compounds nuclearly substituted with a plurality of bromine atoms, the bromobenzene compounds having the mole ratio from $\frac{1}{2}$ to 2/1 to the iodobenzene compounds in the mixture.

4 Claims, No Drawings

PROCESS FOR INCREASING THE TOLERANCE OF X-RAY CONTRAST MEDIA, AND CONTRAST MEDIA OBTAINED THEREBY

This invention relates to X-ray contrast media.

Iodobenzene compounds having several iodine atoms on the benzene nucleus—generally 3 iodine atoms per benzene nucleus—and various other substituents have been used for a long time as X-ray contrast media. Said other substituents are pharmacologically acceptable groups which permit administration of the compounds to humans and animals. Such substituents are generally selected to provide the compounds with sufficient water-solubility to permit administration of said compounds as aqueous solutions.

Multiple procedures have been suggested heretofore to increase the tolerance of the iodobenzene compounds used as X-ray contrast media.

A first type of procedure involved the synthesis of structures with two or three triiodo-benzene nuclei (see, for example, U.S. Pat. No. 3,290,366 and GB No. 1,346,795).

A second type of procedure involved selecting substituents other than iodine atoms in order to achieve an improved tolerance. Particularly, this type of procedure involved non-ionic structures, i.e., which did not exhibit any ionizing substituents such as carboxy groups (see, for example, patents DE-A-No. 2,031,724 and FR-A-No. 2,253,509).

A third type of procedure involved the synthesis of dissymetrical polyiodo- di- or tri-benzene compounds having a single ionizing group (see, for example, U.S. Pat. No. 4,014,986).

Applicant has attempted to solve the problem posed by the increase of the tolerance of iodo benzene compounds in a manner basically different from prior achievements.

Applicant has found that, contrary to what might have been expected, when in known X-ray contrast media part of the iodobenzene compounds is replaced by bromobenzene compounds, not only is the tolerance of the contrast media increased, but also the resulting opacity is of the same order of magnitude.

This latter fact is particularly surprising because, normally, it was to be expected that the partial substitution of the iodobenzene compounds with bromobenzene compounds would lead to a substantial decrease of the opacity. Indeed, it is known that the opacity of an atom to X-rays is substantially proportional to the 3rd power of its atomic number (J. Duheix, V. Bismuth, M. Laval-Jeantet, Traité de Radiodiagnostic, Vol. 1—L'image radiologique, Masson & Cie, 1969). The atomic number of bromine is 35, while that of iodine is 53. Therefore, the opacity imparted by bromine should be three or four times lower. One could thus expect that the presence of bromine atoms instead of part of the iodine atoms would lead to a substantial reduction of the opacity, On the contrary, by partial replacement of the iodobenzene compoundsmedia comprising only iodobenzene compounds. This involves a substantial economic advantage in that bromine is presently much less expensive than iodine.

The present invention relates to X-ray contrast media, having a greater tolerance than that of contrast media comprising solely iodobenzene compounds, together with an opacity of the same order of magnitude as said contrast media, comprising mixtures of benzene compounds nuclearly substituted with a plurality of iodine atoms and of benzene compounds nuclearly substituted with a plurality of bromine atoms.

In such contrast media, the bromobenzene compounds represent advantageously from 1/2 to 2/1 (in moles) of the iodobenzene compounds. In the mixtures, the bromobenzene compounds may be analogs of the iodobenzene compounds or compounds having a different structure.

The invention is quite general, and is applicable to all iodobenzene compounds.

The contrast media of this invention may typically contain mixtures of two or more of the following compounds, one at least being a bromo compound and at least another being a iodo-compound.

I—Compounds of the formula:

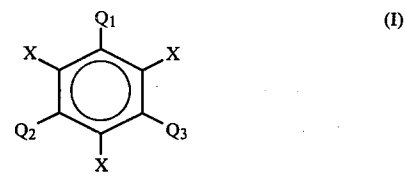

(I)

in which:

the substituents X are selected from I and Br, and $Q_1$, $Q_2$ and $Q_3$ are pharmacologically acceptable groups.

II—Compounds of the formula:

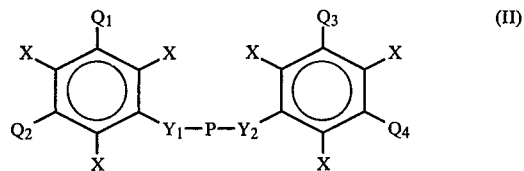

(II)

in which:

the substituents X are selected from I and Br, and $Q_1$, $Q_2$, $Q_3$, $Q_4$, $Y_1$, $Y_2$ and P are pharmacologically acceptable groups.

III—Compounds of the formula:

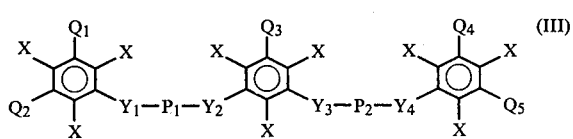

(III)

in which:

the substituents X are selected from I and Br, and $Q_1$, $Q_2$, $Q_3$, $Q_4$, $Q_5$, $Y_1$, $Y_2$, $Y_3$, $Y_4$, $P_1$ and $P_2$ are pharmacologically acceptable groups.

IV—Compounds of the formula:

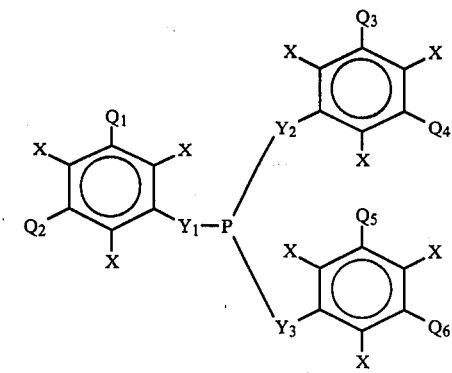

in which:
the substituents X are selected from I and Br, and
$Q_1$, $Q_2$, $Q_3$, $Q_4$, $Q_5$, $Q_6$, $Y_1$, $Y_2$, $Y_3$ and P are pharmacologically acceptable groups.

Examples of groups of types Q, Y, Z and P are given below.

(1) Q type groups
(a) hydrogen
(b) hydrophilic amino groups such as:
A groups of the formula:

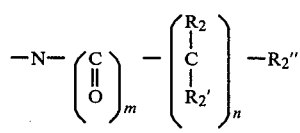

in which:
m = 0, 1 or 2
n = 0 to 6
and the radicals $R_1$, $R_2$, $R_2'$ and $R_2''$ are groups of the formula $(CHZ)_a T$ with
a = 0–5
Z = H or OH
T = H, OH or COOH $-[(CH_2)_b-O(CH_2)_d]_p H$ with
b = 1–5
d = 1–5
p = 1–5
sugar residue.

Typical examples of such groups include groups of the formula:

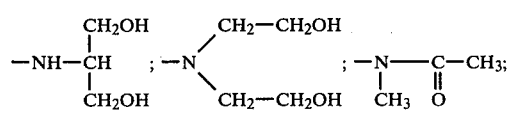

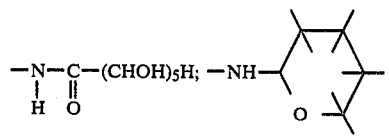

groups of the formula:

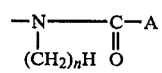

in which
n = 0–3 and
A is a nitrogen containing group such as defined above.
groups of the formula:

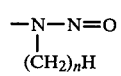

in which
n = 0–3
groups of the formula:

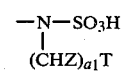

in which
Z = H or OH
T = H or OH
$a_1$ = 0–3
(c) ether or ester groups such as:
$C_{1-6}$ alkoxy groups optionally substituted with carbon groups or amino groups such as the above defined A group;
groups of the formula:

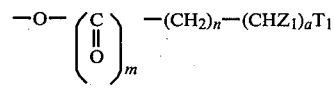

in which
m = 0, 1 or 2
n = 0–6
a = 0–6
$Z_1$ = H, OH or $NH_2$
$T_1$ = H, OH or $NH_2$
groups of the formula

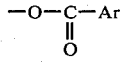

in which Ar represents an aromatic radical
groups of the formula:

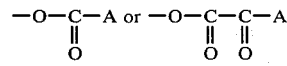

in which A is as previously defined.
(d) sulfonyl groups such as the group —SO₃H
groups of the formula —SO₂—A in which A is as previously defined.
(e) groups with a carbon linkage such as
groups of the formula —(CHZ)ₐT in which
a=0-6
Z=H or OH
T=H or OH
groups of the formula —(CH₂)ₙ—O—Ar in which Ar represents an aromatic radical
groups of the formulae

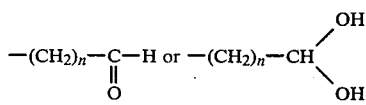

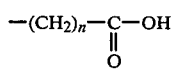

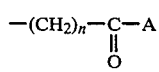

in which
n=0-6
A is as previously defined
groups of the formula

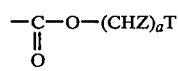

in which
a=0-6
Z=H or OH
T=H or OH
groups of the formula

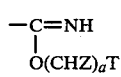

in which
a=0-3
Z=H or OH
T=H or OH
the group —C≡N
(2) Y type groups (divalent)
(a) groups with a carbon linkage such as
groups of the formula

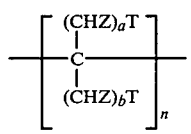

in which a,b = 0-6
Z = H or OH
T = H or OH the group

groups of the formula

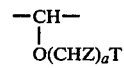

in which
a=0-6
Z=H or OH
T=H or OH
the group

(b) other type groups, such as:
the group

groups of the formula

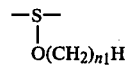

in which
n₁=1-6
the oxy group —O—
groups of the formula

in which a = 0-3
Z,T = H or OH groups of the formula

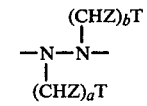

in which
a, b=0-3
Z, T=H or OH
(3) Type P groups
Divalent P groups may be represented by the general formulae

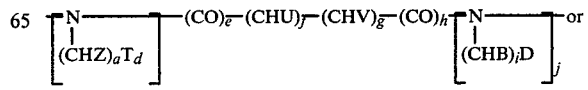

-continued

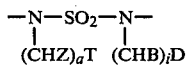

in which:

d, e, h, j = 0, 1 or 2
a, f, g, i = 0–6
Z, U, B, V = H, OH, Br, $(CH_2)_nCOOH$ with n = 0–3
T, D = H or OH Other residues may be intercalated in the bridge, such as groups having the formulae —O—, —S—,

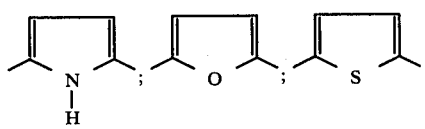

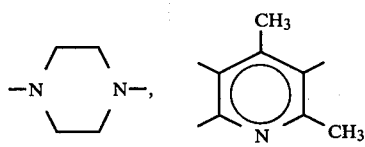

Trivalent P groups may be groups of the formula:

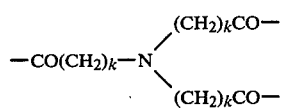

in which k=0–4.

Among the bromo- or iodo-compounds of the formula (I), particularly advantageous classes are those formed by:

1—compounds of the formula:

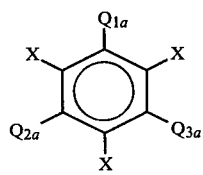   (Ia)

in which:
X is selected from Br and I
$Q_{1a}$ is a —COOH group (generally converted to a salt with a pharmacologically acceptable base)
$Q_{2a}$ is selected from a hydrogen atom; a radical of the formula

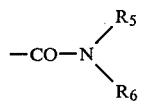

in which $R_5$ and $R_6$ are independently from one another selected from a hydrogen atom, a lower alkyl radical, a lower hydroxyalkyl radical and a lower alkanoyloxy lower alkyl radical; an amino group; and a radical of the formula

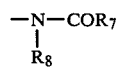

in which $R_7$ is selected from a lower alkyl radical, a lower hydroxyalkyl radical, and a lower alkoxy lower alkyl radical, and $R_8$ is selected from a hydrogen atom, a lower alkyl radical and a lower hydroxyalkyl radical;
$Q_{3a}$ is selected from an amino group and a radical of the formula

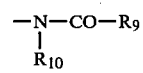

in which $R_9$ and $R_{10}$ have the meanings given for $R_7$ and $R_8$, respectively.

2—compounds of the formula:

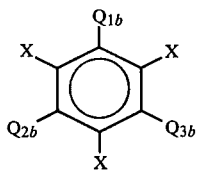   (Ib)

in which:
X is selected from Br and I,
$Q_{1b}$ represents a radical of the formula

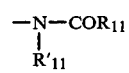

in which $R_{11}$ is a polyhydroxy lower alkyl radical and $R'_{11}$ is selected from a hydrogen atom and a lower alkyl radical,
$Q_{2b}$ represents a radical of the formula

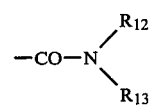

in which $R_{12}$ and $R_{13}$ have the meanings given for $R_5$ and $R_6$, respectively,
$Q_{3b}$ is selected from a radical of the formula

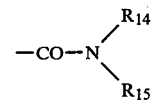

in which $R_{14}$ and $R_{15}$ have the meanings given for $R_5$ and $R_6$, respectively, and a radical of the formula

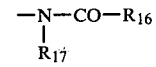

in which $R_{16}$ and $R_{17}$ have the meanings given for $R_7$ and $R_8$, respectively.

3—compounds of the formula:

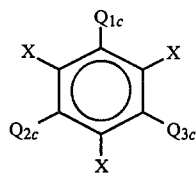

in which:

X is selected from Br and I, $Q_{1c}$ represents a radical of the formula —CON-H—$R_{18}$ in which $R_{18}$ is selected from a sugar residue and a polyhydroxy lower alkyl radical, $Q_{2c}$ represents a radical of the formula

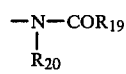

in which $R_{19}$ and $R_{20}$ have the meanings given for $R_7$ and $R_8$, respectively, and $Q_{3c}$ is selected from a radical of the formula

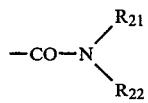

in which $R_{21}$ and $R_{22}$ have the meanings given for $R_5$ and $R_6$, respectively, and a radical of the formula

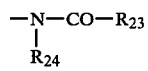

in which $R_{23}$ and $R_{24}$ have the meanings given for $R_7$ and $R_8$, respectively.

Among the compounds of the formula (II), particularly advantageous classes are those formed by:

1—compounds of the formula:

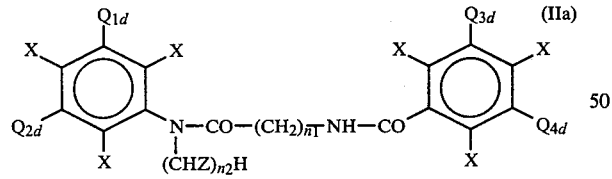

in which:

X is selected from Br and I, $Q_{1d}$ is a —COOH group (generally converted to a salt with a pharmacologically acceptable base), $Q_{2d}$ and $Q_{3d}$ are radicals which have the same meanings as $Q_{2a}$, and $Q_{2d}$ may also represent a radical —CH$_2$OH, $Q_{4d}$ is selected from a group —NH$_2$ and a radical of the formula

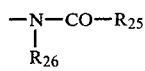

in which $R_{25}$ has the meaning given for $R_7$ and $R_{26}$ is selected from the radicals given for $R_8$ and a lower alkanoyl radical, Z is selected from H and OH $n_1$ is an integer from 1 to 5, $n_2$ is an integer from 0 to 6.

2—compounds of the formula:

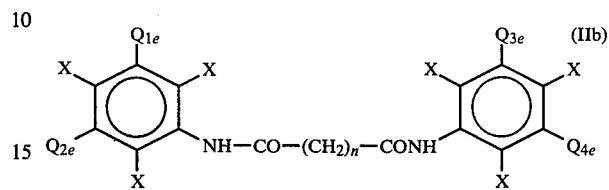

in which:

X is selected from Br and I, $Q_{1e}$ and $Q_{3e}$ are —COOH groups (generally converted to a salt with pharmacologically acceptable bases)

$Q_{2e}$ and $Q_{4e}$ have the meanings given for $Q_{2a}$.

Among the compounds of the formula (IV), a particularly advantageous class is that consisting of compounds of the formula

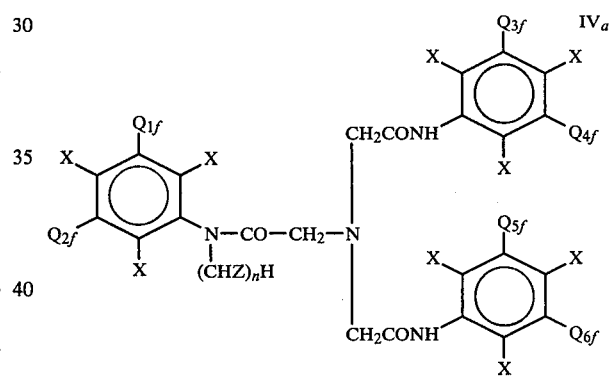

in which:

X is selected from Br and I, $Q_{1f}$ is a —COOH group (generally converted to a salt with a pharmacologically acceptable base), $Q_{2f}$, $Q_{3f}$, $Q_{4f}$, $Q_{5f}$ and $Q_{6f}$ have the meanings given for $Q_{2a}$, Z is selected from H and OH, and n is an integer from 0 to 6.

Another example of compounds of the formula (II) includes compounds of the formula:

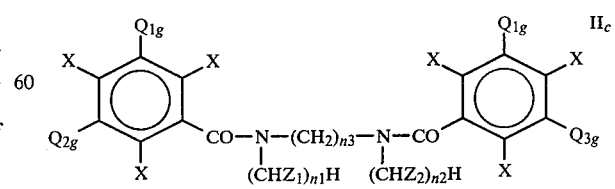

in which:

X is selected from Br and I, $Q_{1g}$ represents a radical of the formula

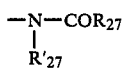

in which R$_{27}$ is a polyhydroxy lower alkyl radical and R'$_{27}$ is selected from a hydrogen atom and a lower alkyl radical, Q$_{2g}$ and Q$_{3g}$ represent independently from one another a radical selected from a radical

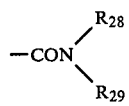

in which R$_{28}$ and R$_{29}$ are independently selected from a hydrogen atom, a lower alkyl radical, a lower hydroxyalkyl radical, and a lower alkanoyloxy lower alkyl radical; an amino group and a radical of the formula

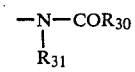

in which R$_{30}$ is selected from a lower alkyl radical, a lower hydroxyalkyl radical and a lower alkoxy lower alkyl radical, and R$_{31}$ is selected from a hydrogen atom, a lower alkyl radical and a lower hydroxyalkyl radical, Z$_1$ and Z$_2$ are independently from one another selected from H and OH, n$_1$ and n$_2$ represent independently from one another an integer from 0 to 6, and n$_3$ represents an integer from 0 to 4.

Another example of compounds of the formula (I) includes compounds of the formula:

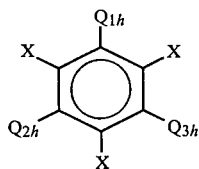

in which:

X is selected from Br and I,

Q$_{1h}$, Q$_{2h}$ and Q$_{3h}$ are independently from one another selected from a —COOH group, a —COOH group converted to a salt with a pharmacologically acceptable base, and a group of the formula

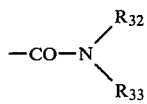

in which R$_{32}$ and R$_{33}$ represent independently from one another a radical selected from a hydrogen atom, a lower alkyl radical, a lower hydroxyalkyl radical, and a lower alkanoyloxy lower alkyl radical.

In the above definitions, the term "lower" applied to the alkyl, alkoxy or alkanoyl radicals refers generally to radicals having 1–6 carbon atoms; in addition, by "hydroxyalkyl" radical is meant a mono- or polyhydroxy alkyl radical.

The new bromobenzene compounds used in the present invention may be prepared by methods used to prepare polyiodo analogs. For this purpose, the conventional bromination, alkylation, acylation (by condensation of an acid chloride with an amine or an alcohol) and salt-forming reactions, widely described for the polyiodo analogs, may be used.

The iodobenzene compounds are widely described in the literature and a number of these are commercially available.

Examples of iodobenzene compounds of the formula (Ia) include diatrizoic acid, iothalamic acid, metrizoic acid, acetrizoic acid, iodamide and ioxitalamic acid.

Ioglunide is an example of an iodobenzene compound of the formula (I$_b$).

Metrizamide is an example of an iodobenzene compound of the formula (I$_c$).

Ioxaglic acid is an example of an iodobenzene compound of the formula (II$_a$)

Examples of iodobenzene compounds of the formula (II$_b$) include iocarmic acid, adipiodone and ioglycamic acid.

The following Examples illustrate the preparation of bromobenzene compounds.

EXAMPLE I

Preparation of 2,4,6-tribromo-3-N-methylcarbamoyl-5-N-methyl-N-acetylamino-benzoic acid

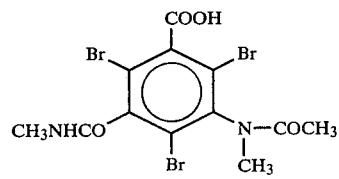

(1) Preparation of 2,4,6-tribromo-3-N-methylcarbamoyl-5-amino-benzoic acid

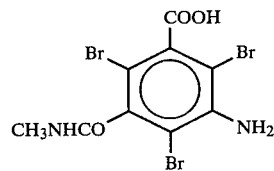

194 g (1 mole) 3-N-methylcarbamoyl-5-amino-benzoic acid are suspended in 4 liters water and 820 ml concentrated hydrochloric acid. Bromine (230 ml; 9 moles) is added dropwise thereto. Stirring is continued for 24 hours at room temperature, after which the precipitate is suction filtered, washed with 2 liters water at 90° C. and dried at 110° C. for 24 hours, to give 410 g crude acid (Yield: 95%).

Purity control:

TLC in eluent benzene/MEK/formic acid 60:25:20

Rf of the starting material: 0.1

Rf of the bromo compound: 0.7

Purity by bromine titration: 98%.

(2) Preparation of 2,4,6-tribromo-3-N-methylcarbamoyl-5-N-acetylamino-benzoic acid

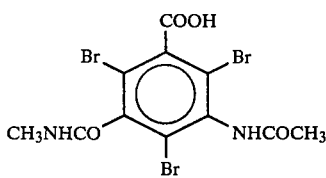

(a) Condensation 2,4,6-Tribromo-3-N-methylcarbamoyl-5-amino-benzoic acid (230 g; 0.5 mole) is suspended in acetic anhydride (200 ml) and acetic acid (100 ml). Concentrated sulfuric acid (60 ml) is added dropwise thereto, while maintaining the temperature below 55°–60° C. When addition of the sulfuric acid is complete, the mixture is stirred at 55° C. for 1 hour. The resulting solution is poured over 1 liter water+ice. Precipitation occurs. The material is stirred at room temperature for 24 hours, after which it is suction filtered, washed with water and dried in an oven at 80° C. for 16 hours, to give 240 g crude acid (Yield: 100%).

(b) Purification

Purification is effected by crystallization of the ammonium salt.

The crude acid (42 g) is suspended in 45 ml water. 10N ammonia is added until dissolution is complete (i.e., pH=7–8). The mixture is stirred at room temperature for 24 hours. Crystallization occurs. The resulting material is suction filtered and clarified with 10 ml water. The precipitate is dissolved in 500 ml water at 90° C. and is charcoaled twice with charcoal 3SA at 80° C. for 2 hours. The product is precipitated with 1/10 hydrochloric acid, suction filtered, washed with water and dried overnight at 80° C., to give 30 g of the desired product in a yield of 71%.

Purity control:

TLC in eluent benzene/MEK/formic acid 60:25:20

Rf of the starting material: 0.7

Rf of the acetylated product: 0.35 in eluent butanol/acetic acid/water 60:11:25

Rf of the starting material: 0.75

Rf of the acetylated product: 0.3

Purity by bromine titration: 100%

Purity by titration with sodium hydroxide: 99%.

(3) Preparation of 2,4,6-tribromo-3-N-methylcarbamoyl-5-N-methyl-N-acetylamino-benzoic acid (a) Methylation

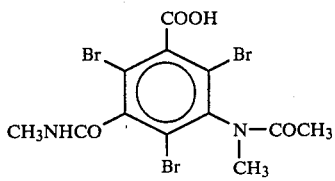

2,4,6-Tribromo-3-N-methylcarbamoyl-5-N-acetylaminobenzoic acid (189 g; 0.4 mole) is dissolved in 5N sodium hydroxide (184 ml; 0.92 mole). Methyl iodide (32.4 ml; 0.52 mole) is added and the mixture is stirred at room temperature for 24 hours. Completion of the reaction is controlled by TLC in eluent butanol/acetic acid/water 50:11:25. The solution is poured over water (300 ml) and concentrated hydrochloric acid (75 ml). Precipitation occurs. The material is allowed to crystallize for 5 hours and is then suction filtered. The precipitate is taken up into 500 ml water. 10N Sodium hydroxide is added until dissolution is complete, and the pH is then adjusted to a value of 4 by addition of acetic acid. The solution is decolorized by addition of 1 ml of a sodium bisulfite solution. The material is precipitated in acidic medium and is then suction filtered, washed with water and dried at 80° C. for 24 hours, to give 157 g of the desired product, in a yield of 81% for the methylation.

(b) Purification

Purification is effected by recrystallization from methanol-water.

The crude acid (100 g) is suspended in 500 ml water. The suspension is heated at 80° C., and 95% ethanol (130 ml) is slowly added until dissolution is complete. The material is filtered and allowed to crystallize with stirring for 24 hours, after which it is suction filtered, clarified with water-ethanol and dried in an oven at 80° C. for 24 hours, to give 62.8 g of product which is dissolved in 200 ml water and sodium hydroxide. The pH is adjusted to 4–5 with acetic acid and the material is charcoaled twice. It is then filtered, and made acidic with concentrated hydrochloric acid, after which it is suction filtered, washed with water and dried at 80° C. for 24 hours, to give 50 g pure product (Yield: 50%).

Purity control:

TLC in eluent butanol/acetic acid/water 50:11:25

Rf of the starting material: 0.3

Rf of the methylated product: 0.25 and 0.35.

Purity by titration with sodium methoxide: 97%

Purity by bromine titration: 97%.

EXAMPLE II

Preparation of 2,4,6-tribromo-3-N-hydroxyethylcarbamoyl-5-N-methyl-N-acetylamido-benzoic acid

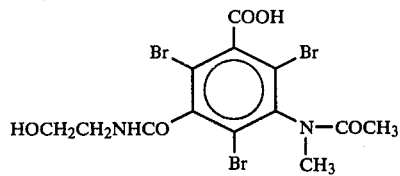

(1) Preparation of 2,4,6-tribromo-3-N-hydroxyethylcarbamoyl-5-amino-benzoic acid

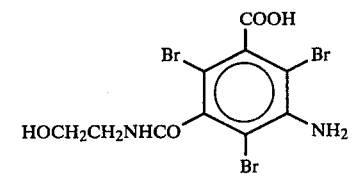

2,4,6-Tribromo-3-N-hydroxyethylcarbamoyl-5-amino-benzoic acid is prepared as in Example I-1 from 3-N-hydroxyethyl carbamoyl-5-amino-benzoic acid.

Yield: 96.5%

Purity control:

TLC in eluent benzene/MEK/formic acid 60:25:20

Rf of the starting material: 0.05

Rf of the bromo compound: 0.55

Purity by bromine titration: 100%.

(2) Preparation of 2,4,6-tribromo-3-N-hydroxyethylcarbamoyl-5-N-acetylamino-benzoic acid

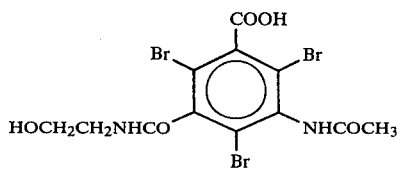

2,4,6-Tribromo-3-N-hydroxyethylcarbamoyl-5-N-acetylamino-benzoic acid is prepared as in Example I-2 from 2,4,6-tribromo-3-N-hydroxyethylcarbamoyl-5-aminobenzoic acid.

Yield (acetylation): 75.5%
Yield (purification): 65.5%
Purity control:
TLC in eluent benzene/MEK/formic acid 60:25:20
Rf of the starting material: 0.55
Rf of the acetylated product: 0.25
Purity by bromine titration: 101%
Purity by titration with sodium methoxide: 100%.

(3) Preparation of 2,4,6-tribromo-3-N-hydroxyethylcarbamoyl-5-N-methyl-N-acetylamino-benzoic acid

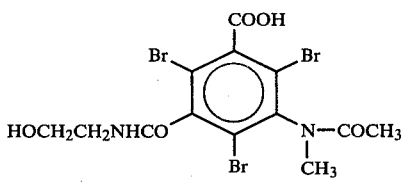

2,4,6-Tribromo-3-N-hydroxyethylcarbamoyl-5-N-methyl-N-acetylamino-benzoic acid is prepared as in Example I-3 from 2,4,6-tribromo-3-N-hydroxyethylcarbamoyl-5-N-acetylamino-benzoic acid.

Overall yield (methylation and purification): 20%
Purity control:
TLC in eluent benzene/MEK/formic acid 60:25:20
Rf of the starting material: 0.25
Rf of the methylated product: 0.25
TLC in eluent butanol/CH$_3$COOH/water 50:11:25
Rf of the starting material: 0.20
Rf of the methylated product: 0.18–0.32
Purity by titration with sodium methoxide: 98%
Purity by bromine titration: 104%.

EXAMPLE III

Preparation of 2,4,6-tribromo-3-N-methyl-N-acetylaminobenzoic acid

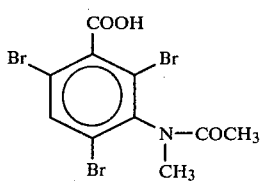

(1) Preparation of 2,4,6-tribromo-3-aminobenzoic acid

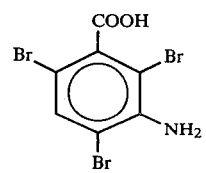

2,4,6-Tribromo-3-amino-benzoic acid is prepared as in Example I-1 from 3-amino-benzoic acid.
Yield: 95.2%.
Purity control:
TLC in eluent benzene/MEK/formic acid 60:25:20
Rf of the starting material: 0.2
Rf of the bromo compound/0.85
Purity by bromine titration: 99%

(2) Preparation of 2,4,6-tribromo-3-N-acetylaminobenzoic acid

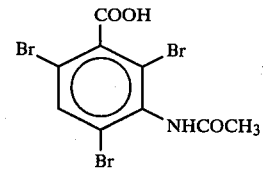

2,4,6-Tribromo-3-N-acetylamino-benzoic acid is prepared as in Example I-2 from 2,4,6-tribromo-3-N-acetylamino-benzoic acid.
Yield: 84.5%
Purity control:
TLC in eluent benzene/MEK/formic acid 60:25:20
Rf of the starting material: 0.85
Rf of the acetylated product: 0.6
Purity by titration with sodium methoxide: 97%

(3) Preparation of 2,4,6-tribromo-3-N-methyl-N-acetylamino-benzoic acid

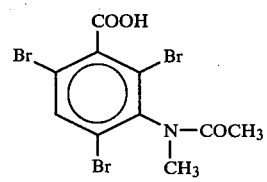

2,4,6-Tribromo-3-N-methyl-N-acetylamino-benzoic acid is prepared as in Example I-3 from 2,4,6-tribromo-3-N-acetylamino-benzoic acid.
Overall yield (methylation and purification): 64.5%
Purity control:
TLC in eluent benzene/MEK/Formic acid 60:25:20
Rf of the starting material: 0.6
Rf of the methylated product: 0.75
TLC in eluent butanol/CH$_3$COOH/water 50:11:25
Rf of the starting material: 0.45
Rf of the methylated product: 0.55
Purity by titration with sodium methoxide: 98%
Purity by bromine titration: 99%

EXAMPLE IV

Preparation of 2,4,6-tribromo-3-amino-5-N-methyl-N-acetylamino-benzoic acid

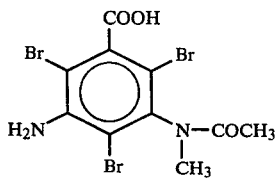

(1) Preparation of 2,4,6-tribromo-3-amino-5-N-acetylamino-benzoic acid

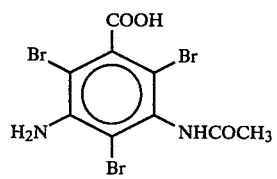

2,4,6-Tribromo-3-amino-5-N-acetylamino-benzoic acid is prepared as in Example I-1 from 3-amino-5-N-acetylamino-benzoic acid.

Yield: 95%
Purity control:
TLC in eluent benzene/MEK/formic acid 60:25:20
Rf of the starting material: 0.07
Rf of the bromo compound/0.65
Purity by bromine titration: 97%.

(2) Preparation of 2,4,6-tribromo-3-amino-5-N-methyl-N-acetylamino-benzoic acid

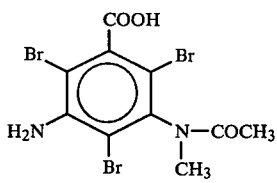

2,4,6-Tribromo-3-amino-5-N-methyl-N-acetylamino-benzoic acid is prepared as in Example I-3, from 2,4,6-tribromo-3-amino-5-N-acetylamino-benzoic acid.

Yield: 81%
Purity control:
TLC in eluent butanol/acetic acid/water 50:11:25
Rf of the starting material: 0.4
Rf of the methylated product: 0.32 and 0.47
Purity by bromine titration: 98%
Purity by titration with sodium methoxide: 101%.

EXAMPLE V

Preparation of 5,5'-adipoyldiimino-bis(2,4,6-tribromo-5-amino-N-methyl-isophthalamic) acid

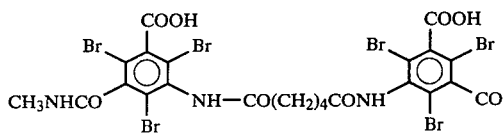

(a) Condensation 2,4,6-Tribromo-3-N-methylcarbamoyl-5-amino-benzoic acid (150 g; 0.348 mole) is dissolved in 520 ml dimethyl acetamide. Adipoyl chloride (25.5 ml; 0.2 mole) is added dropwise while maintaining the temperature between 20° and 25° C. The material is stirred at room temperature for 12 hours.

Completion of the reaction is controlled by TLC.

The solution is poured over 900 ml water. Precipitation occurs. Stirring is maintained for 16 hours, after which the material is suction filtered, washed with water and dried at 60° C. for 24 hours, to give 135 g of the desired product (Yield: 80%).

(b) Purification

Purification is effected by crystallization of the ammonium salt.

The product (135 g) is suspended in 135 ml water, and 10N ammonia is added until dissolution is complete (pH 7-8). Stirring is maintained for 24 hours. Crystallization occurs. After suction filtering and clarifying with 20 ml water, the precipitate is dissolved in 500 ml water and treated with charcoal 3SA. The material is filtered, made acidic with concentrated hydrochloric acid; it is then suction filtered, washed with water and dried in an oven at 80° C. for 16 hours, to give 58.9 g purified product (yield: 43.5% for the purification).

Purity control:
TLC in eluent benzene/MEK/formic acid 60:25:10
Rf of the starting material: 0.7
Rf of the condensed product: 0.45
Purity by bromine titration: 104%
Purity by titration with sodium methoxide: 93%
Purity by titration with tetrabutylammonium: 104%

EXAMPLE VI

Preparation of 5,5'-adipoyldiimino-bis-(2,4,6-tribromo-3-amino-benzoic) acid

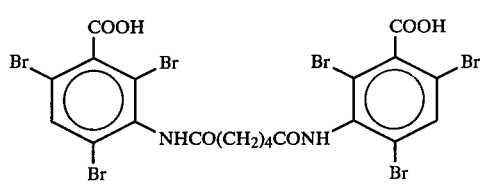

5,5'-Adipoyldiimino-bis-(2,4,6-tribromo-3-amino-benzoic) acid is prepared as in Example V, from 2,4,6-tribromo-3-amino-benzoic acid.

Condensation yield: 100%
Purification yield: 100%
Purity control:
TLC in eluent benzene/MEK/formic acid 60:25:10
Rf of the starting material: 0.85
Rf of the condensed product: 0.5
Purity by bromine titration: 99%
Purity by titration with sodium methoxide: 101%.

EXAMPLE VII

Preparation of 2,4,6-tribromo-3-N-hydroxyethylcarbamoyl-5-(2,4,6-tribromo-3-N-methylcarbamoyl-5-N-methyl-N-acetylamino-benzoyl)-glycylamino-benzoic acid

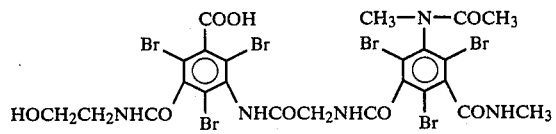

(1) Preparation of 2,4,6-tribromo-3-N-hydroxyethylcarbamoyl-5-aminoacetamido-benzoic acid (a) Preparation of 2,4,6-tribromo-3-N-phthalimidoacetoxyethylcarbamoyl-5-phthalimidoacetylamino-benzoic acid

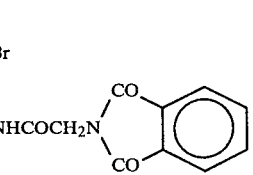

2,4,6-Tribromo-3-N-hydroxyethylcarbamoyl-5-amino-benzoic acid (322 g; 0.7 mole) is dissolved in 600 ml dimethylacetamide. Phthalylglycine acid chloride (392 g; 1.75 mole) is added portionwise thereto. After stirring at room temperature for 48 hours, the solution is poured over 2 liters water at 70° C. Precipitation occurs; stirring is continued for a further half-hour and the material is suction filtered.

The product is used without drying and without further purification in the subsequent step.

Control:
TLC in eluent benzene/MEK/formic acid 60:25:20
Rf 0.7 (starting material: Rf 0.55).

(b) Preparation of 2,4,6-tribromo-3-N-hydroxyethylcarbamoyl-5-aminoacetamido-benzoic acid

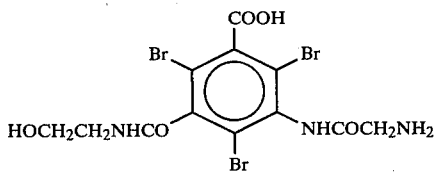

The product obtained previously is suspended in 2.4 liters water and 204 ml hydrazine hydrate. It is heated at 90° C. for 1 hour, and stirring is maintained at room temperature for 48 hours. Crystallization occurs. The material is suction filtered and clarified with water, to give a product which contains 10–15% phthalhydrazide. The product is taken up into 1 liter water and 100 ml concentrated sulfuric acid; the mixture is heated to 90° C. The insoluble is filtered off and the pH is adjusted to 3–4 with ammonia. Crystallization is allowed to proceed overnight at room temperature.

Suction filtering, washing with water and drying in an oven give 175 g of product (Yield 48.5%).

Purity control:
TLC in eluent benzene/MEK/formic acid 60:25:20
Rf 0.05 (orange-yellow spot on development with ninhydrin)
There remains about 1% phthalhydrazide at Rf 0.75.
Purity by bromine titration: 98%.

(2) Preparation of 2,4,6-tribromo-3-N-methylcarbamoyl-5-N-methyl-N-acetylamino-benzoic acid chloride

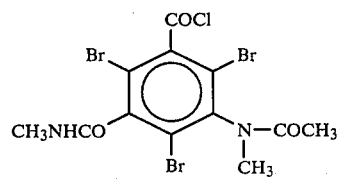

2,4,6-Tribromo-3-N-methylcarbamoyl-5-methyl-N-acetylamino-benzoic acid (296 g; 0.59 mole) is suspended in 600 ml thionyl chloride. The suspension is heated at 80° C. with stirring for 3 hours. A solution is obtained; the excess thionyl chloride is evaporated in vacuo. The pasty residue is taken up into isopropyl ether (500 ml) and is stirred at room temperature for 24 hours. Crystallization occurs. After suction filtering, clarifying with isopropyl ether, the precipitate is washed with acetone (250 ml) at room temperature for 24 hours, with stirring. It is then suction filtered, clarified with 50 ml acetone, after which the product is dried in vacuo, to give 150 g of light beige product (Yield: 50.5%).

Purity control:
TLC (after reaction with excess monoethanolamine in dimethylacetamide) in eluent benzene/MEK/formic acid 60:25:20
Rf of the starting material 0.57
Rf of the monoethanolamine condensation product 0.35
Acid chloride titration with propylamine: 105%.

(3) Preparation of 2,4,6-tribromo-3-N-hydroxyethylcarbamoyl-5-(2,4,6-tribromo-3-N-methylcarbamoyl-5-N-methyl-N-acetylamino-benzoyl)-glycylamino-benzoic acid.

(a) Condensation 2,4,6-Tribromo-3-N-hydroxyethylcarbamoyl-5-N-aminoacetamido-benzoic acid (135 g; 0.296 mole) is suspended in a mixture of dimethylacetamide (300 ml) and triethylamine (107 ml; 0.74 mole). 2,4,6-Tribromo-3-N-methylcarbamoyl-5-N-methyl-N-acetylamino-benzoic acid chloride (150 g; 0.296 mole) is added to the suspension, and the mixture is then stirred at 45° C. for 3 hours. Completion of the reaction is controlled by TLC: there is less than 3% starting material left. The solution is poured over 1 liter water and is then made acidic with concentrated hydrochloric acid. A slight precipitate is formed; stirring is continued at room temperature for 8 days.

The resulting material is suction filtered, washed with water and dried at 60° C. for 24 hours, to give 68.2 g of product (Yield: 24%).

(b) Purification

The product (68.2 g) is dissolved in 130 ml refluxing absolute ethanol, and is then allowed to crystalize at room temperature for 24 hours. After suction filtering and clarifying, the product is dissolved in 200 ml of water and sodium hydroxide. The pH is adjusted to 4–5 with acetic acid and the material is charcoaled twice, after which it is filtered and made acidic with concentrated hydrochloric acid.

43 g of product are obtained after suction filtering, washing with water and drying at 60° c. for 24 hours (Yield: 63% for the purification).

Purity control:
TLC in eluent benzene/MEK/formic acid 60:25:20
Rf of the amine: 0.07
Rf of the acid corresponding to the acid chloride: 0.7.
Rf of the condensed product: 0.4
Purity by bromine titration: 100%
Purity by titration with sodium methoxide: 97%.

EXAMPLE VIII

Preparation of
2,4,6-tribromo-3-N-hydroxyethylcarbamoyl-5-(2,4,6-tribromo-3-N-hydroxyethylcarbamoyl-5-N-methyl-N-acetylamino-benzoyl)-glycylamino-benzoic acid

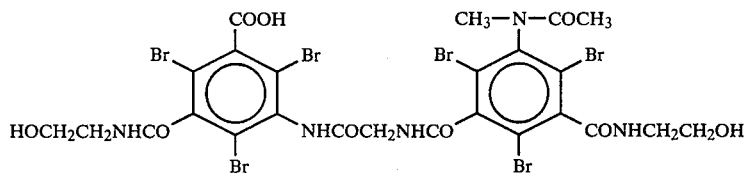

(1) Preparation of 2,4,6-tribromo-3-N-acetoxyethylcarbamoyl-5-N-methyl-N-acetylamino-benzoic acid

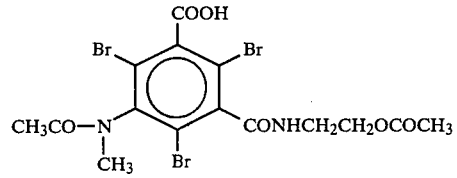

2,4,6-Tribromo-3-N-hydroxyethylcarbamoyl-5-N-methyl-N-acetylamino-benzoic acid (270 g (0.52 mole) is suspended in 1.3 liter dioxan. Acetyl chloride (78 ml; 1.04 mole) is added thereto and the mixture is heated at 80° C. for 8 hours. The dioxan is removed by evaporation in vacuo, to give 290 g of product (Yield: 98.6%). This product is used without further purification.
Purity control:
TLC in eluent benzene/MEK/formic acid 60:25:20
Rf of the starting material: 0.25
Rf of the O-acetylated product: 0.40.

(2) Preparation of 2,4,6-tribromo-3-N-acetoxyethylcarbamoyl-5-N-methyl-N-acetylamino-benzoic acid chloride

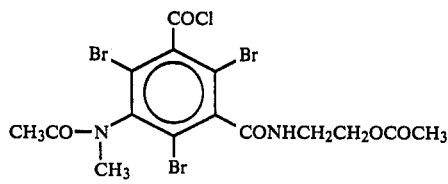

2,4,6-Tribromo-3-N-acetoxyethylcarbamoyl-5-N-methyl-N-acetylamino-benzoic acid (290 g; 0.52 mole) is suspended in 500 ml thionyl chloride. The suspension is heated at 80° C. for 4 hours. The excess thionyl chloride is then removed in vacuo.

300 g of product are obtained after drying (Yield: 100%). This product is used without further purification.

(3) Condensation

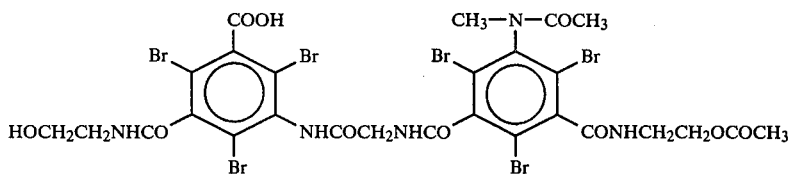

2,4,6-Tribromo-3-N-hydroxyethylcarbamoyl-5-(2,4,6-tribromo-3-N-acetoxyethylcarbamoyl-5-N-methyl-N-acetylamino-benzoyl)-glycylamino-benzoic acid is prepared as in Example VII, from 2,4,6-tribromo-3-N-hydroxyethylcarbamoyl-5-aminoacetamido-benzoic acid and 2,4,6-tribromo-3-N-acetoxyethylcarbamoyl-5-N-methyl-N-acetylamino-benzoic acid chloride.
Yield of the condensation: 62.5%.
The product is used without further purification.
(4) Saponification
2,4,6-Tribromo-3-N-hydroxyethylcarbamoyl-5-(2,4,6-tribromo-3-N-acetoxyethylcarbamoyl-5-N-methyl-N-acetylamino-benzoyl)-glycylamino-benzoic acid (146 g; 0.138 mole) is dissolved in 2N sodium hydroxide (270 ml). The solution is heated at 45° C. for 2 hours. It is adjusted to pH 6–7 with hydrochloric acid and is then charcoaled twice. It is then filtered and precipitated in acidic medium (pH 1). The resulting material is suction filtered, clarified and dried in an oven at 60° C. for 20 hours, to give 54 g of the desired product (Yield: 24%).
Purity control:
TLC in eluent benzene/MEK/formic acid 60:25:20
Rf of the starting material: 0.1
Rf of the saponified product: 0.05
(5) Purification
Purification is effected by crystallization from isopropanol.

The crude product (54 g) is suspended in 54 ml isopropanol. The suspension is heated at 80° C. for 2 hours. It is then stirred overnight at room temperature. Crystallization occurs. After suction filtering and clarifying with isopropanol, the product is washed with water, after which it is dried in an oven at 80° C. for 16 hours, to give 21 g of the desired product (Purification yield: 34%).

Purity control:

TLC in eluent benzene/MEK/formic acid 60:25:20

Rf 0.05 in eluent butanol/acetic acid/water 50:11:25

Rf 0.2 and 0.3.

EXAMPLE IX

Preparation of 2,4,6-tribromo-3-N-methylcarbamoyl-5-(2,4,6-tribromo-3-N-methyl-N-acetylamino-benzoyl)-glycylamino-benzoic acid

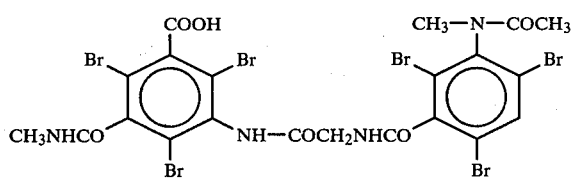

(1) Preparation of 2,4,6-tribromo-3-N-methylcarbamoyl-5-aminoacetylamino-benzoic acid

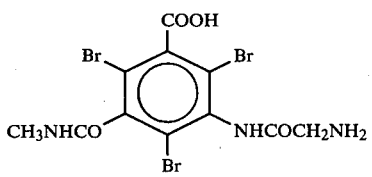

This acid is prepared as in Example VII-1 from 2,4,6-tribromo-3-N-methylcarbamoyl-5-aminobenzoic acid.

Yield obtained: 45%

Purity control:

TLC in eluent benzene/MEK/formic acid 60:25:20

Rf 0.1 in eluent butanol/acetic acid/water 50:11:25

Rf 0.07

Purity by bromine titration: 96%.

(2) Preparation of 2,4,6-tribromo-3-N-methyl-N-acetylamino-benzoic acid chloride

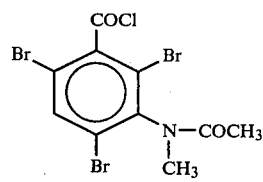

The compound is prepared as in Example VII-2, using 2,4,6-tribromo-3-N-methyl-N-acetyl-amino-benzoic acid Yield obtained: 85%

Purity control:

TLC (after reaction with excess monoethanolamine in dimethylacetamide) in eluent benzene/MEK/formic acid 60:25:20

Rf of the starting material: 0.7

Rf of the monoethanolamine condensation product: 0.5

Preparation of 2,4,6-tribromo-3-N-methylcarbamoyl-5-(2,4,6-tribromo-3-N-methyl-N-acetylaminobenzoyl)-glycylamino-benzoic acid

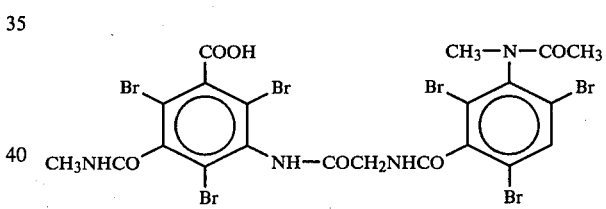

2,4,6-Tribromo-3-N-methylcarbamoyl-5-(2,4,6-tribromo-3-N-methyl-N-acetylamino-benzoyl)-glycylamino-benzoic acid is prepared as in Example VII, from 2,4,6-tribromo-3-N-methylcarbamoyl-5-aminoacetamido-benzoic acid and 2,4,6-tribromo-3-N-methyl-N-acetylamino-benzoic acid chloride.

Condensation yield: 85%

Purification yield: 13.5%

Purity control:

TLC in eluent benzene/MEK/formic acid 60:25:20

Rf of the amine: 0.05

Rf of the acid corresponding to the acid chloride: 0.85

Rf of the condensed product: 0.5

Purity by bromine titration: 96%

Purity by titration with sodium methoxide: 103%.

EXAMPLE X

Preparation of 2,4,6-tribromo-3-N-methylcarbamoyl-5-bis-[(2,4,6-tribromo-3,5-bis(N-hydroxyethylcarbamoyl)phenyl)-carbamoyl-methyl]amino-acetamido-benzoic acid

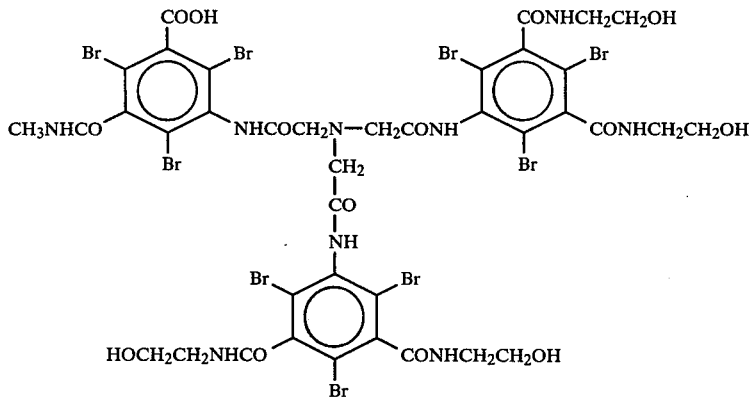

(1) Preparation of 2,4,6-tribromo-3,5-bis(hydroxyethylcarbamoyl)-chloroacetanilide

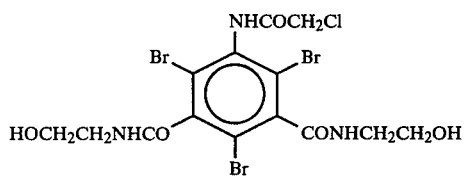

(a) Preparation of 2,4,6-tribromo-5-amino-isophthalic acid

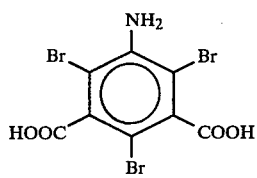

This acid is prepared as in Example I-1 from 3-amino-isophthalic acid.
Yield: 86.5%
Purity control:
TLC in eluent benzene/MEK/formic acid 60:25:20
Rf of the starting material: 0.1
Rf of the bromo compound: 0.8
Purity by bromine titration: 99%.

(b) Preparation of 2,4,6-tribromo-5-amino-isophthalic acid chloride

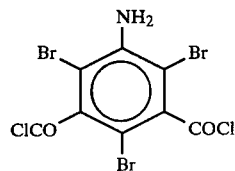

2,4,6-Tribromo-5-amino-isophthalic acid (729 g; 1.73 mole) is suspended in 1800 ml thionyl chloride. The suspension is heated at 80° C. for 8 hours. Excess thionyl chloride is removed in vacuo and the concentrate is taken up into 1 liter isopropyl ether. Crystallization occurs. The material is suction filtered, clarified with isopropyl ether, and dried in vacuo, to give 465 g of the desired product (Yield: 60%).
Purity control:
TLC in eluent benzene/MEK/formic acid 60:25:20
Rf of the starting acid: 0.8
Rf of the product after condensation with monoethanolamine: 0.4
Purity by titration of the acid chloride with propylamine: 105%.

(c) Preparation of 2,4,6-tribromo-3,5-bis(hydroxyethylcarbamoyl)-aniline

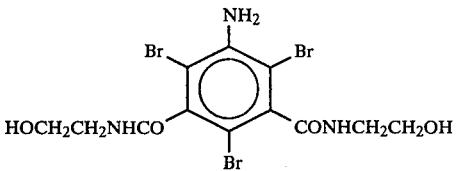

2,4,6-Tribromo-5-amino-isophthalic acid chloride (184 g; 0.404 mole) is dissolved in 180 ml dimethylacetamide. Monoethanolamine (145 ml; 2.4 moles) is added dropwise while maintaining the temperature between 20° and 25° C. The reaction mixture is stirred at room temperature for 16 hours. It is then poured over 1 liter ice-water. Precipitation occurs. After stirring 24 hours at room temperature, the material is suction filtered, washed with water and dried at 80° C. for 16 hours, to give 168 g of product (Yield: 84%).
Purity control:
TLC in eluent benzene/MEK/formic acid 60:25:20
Rf 0.4
Purity by bromine titration: 98%.

(d) Preparation of 2,4,6-tribromo-3,5-bis(hydroxyethylcarbamoyl)-chloroacetanilide
Condensation
The above product (515 g; 1.02 mole) is dissolved in 775 ml dimethylacetamide.
Chloroacetyl chloride (377 ml; 4.7 moles) is added dropwise thereto while maintaining the temperature between 20° and 30° C., and the reaction mixture is then stirred at room temperature for 16 hours and poured over 4.5 liters ice-water. Precipitation occurs. The material is suction filtered and clarified with water. The product is used without drying.
Purity control:
TLC in eluene benzene/MEK/formic acid 60:25:20
Rf of the starting material: 0.4

Rf of the condensed product: 0.85

Saponification

The above product is suspended in 2N sodium hydroxide (1750 ml) and is then stirred at room temperature for 16 hours. The reaction mixture is made acidid with hydrochloric acid (pH 1), suction filtered, washed with water and dried at 80° C. for 16 hours, to give 215 g of the desired product (Yield: 36%).

Purity control:

TLC in eluent benzene/MEK/formic acid 60:25:20

Rf starting material: 0.4

Rf of the chloroacetylated product: 0.2

Purity by bromine titration: 99%

Purity by chlorine titration: 105%.

(2) Preparation of 2,4,6-tribromo-3-N-methylcarbamoyl-5-bis[(2,4,6-tribromo-3,5-bis(N-hydroxyethylcarbamoyl)-phenyl)carbamoyl-methyl]amino-acetamido-benzoic acid (a) Condensation A solution of 2,4,6-tribromo-3-N-methylcarbamoyl-5-amino-acetamido-benzoic acid (10 g; 0.02 mole) in 1N sodium hydroxide (18 ml) is mixed with the solution of 2,4,6-tribromo-3,5-bis(hydroxyethylcarbamoyl)-chloroacetanilide (23.2 g; 0.04 mole) in 1N sodium hydroxide (40 ml).

After heating at 85° C. for 1 hour, 1N sodium hydroxide (18 ml) is again added, and heating is maintained at 85° C. for 20 hours. The solution is cooled to 20° C. and made acidic to pH 1 with concentrated hydrochloric acid. A gum is formed, which crystallizes after 16 hours at room temperature. It is suction filtered, washed with water and dried in an oven at 60° C. for 24 hours, to give 29 g crude acid.

(b) Purification

The 29 g crude acid are suspended in 60 ml water and the suspension is adjusted to pH 7 with sodium hydroxide. The insoluble is filtered off and the material is made acidic to a pH to 1 or less, with concentrated hydrochloric acid. The precipitate is suction filtered and washed with water.

The precipitate is suspended in 10 ml water and ammonia is added until neutral. Ammonium chloride (2 g) is added to the solution which is then stirred at room temperature for 48 hours. Crystallization occurs. The reaction mixture is suction filtered. The precipitate is dissolved in 50 ml water and charcoaled twice. The product is precipitated with hydrochloric acid. The precipitate is suction filtered, washed with water and dried, to give 5.2 g purified product.

Purity control:

TLC in eluent butanol/acetic acid/water 50:11:25

Rf of the starting chloro compound: 0.65

Rf of the starting amino compound: 0.07

Rf of the condensation product: 0.2

Purity of bromine titration: 98.7%

Purity by titration with sodium methoxide: 95%.

EXAMPLE XI

Preparation of 2,4,6-tribromo-3-(N-methyl-acetamido)-5-(N-hydroxyethylcarbamoyl)-N-gluconyl aniline

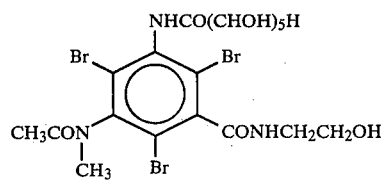

(1) Preparation of 2,4,6-tribromo-3-N-methyl-N-acetylamino-5-amino-benzoic acid chloride

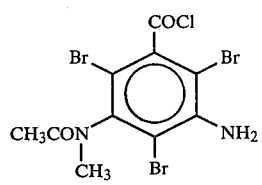

2,4,6-Tribromo-3-N-methyl-N-acetyl-5-amino-benzoic acid (200 g; 0.446 mole) is suspended in 200 ml isopropyl ether. Thionyl chloride (200 ml) is added dropwise thereto. The reaction mixture is stirred at 80° C. for 4 hours and then overnight at room temperature. The mixture is evaporated with a rotary evaporator to give a residue which is taken up into 400 ml isopropyl ether. This is stirred at room temperature for 24 hours. Crystallization occurs. After suction filtering, clarifying and drying at 40° C. for 24 hours, there are obtained 165 g of product (Yield: 79.3%).

Purity control:

TLC in eluent benzene/MEK/formic acid 60:25:20

Rf of the starting material: 0.7–0.8

Rf of the acid chloride: 0.5 (after condensation with monoethanolamine)

Purity by titration with propylamine: 90.5%.

(2) Preparation of 2,4,6-tribromo-3-N-hydroxyethylcarbamoyl-5-N-methyl-N-acetylamino-aniline

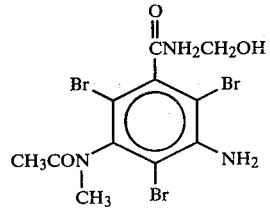

2,4,6-Tribromo-3-N-methyl-N-acetylamino-5-amino-benzoic acid chloride (65.3 g; 0.140 mole) is dissolved in 100 ml dimethylacetamide. Ethanolamine (25.2 ml; 0.42 mole) is added dropwise, while cooling if necessary so that the temperature does not exceed 25° C. The reaction mixture is stirred at room temperature for 2 days.

The solution is poured over a mixture of water (400 ml) and ice (80 g). A precipitate is formed. Stirring is maintained for 48 hours, after which the material is suction filtered, washed, clarified and dried, to give 56.4 g of the desired product (Yield: 82.5%).

Purity control:

TLC in eluent benzene/MEK/formic acid 60:25:20

Rf of the starting material: 0.7–0.8
Rf of the condensed product: 0.55.

(3) Preparation of 2,4,6-tribromo-3-N-acetoxyethylcarbamoyl-5-N-methyl-N-acetylamino-aniline

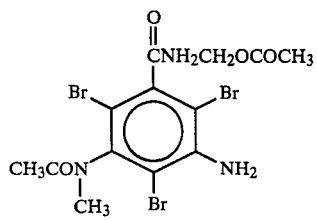

2,4,6-Tribromo-3-N-hydroxyethylcarbamoyl-5-N-methyl-N-acetylamino-aniline (56.4 g; 0.115 mole) is suspended in a mixture of 74.8 ml acetic acid and 0.78 ml sulfuric acid. This is stirred at 80° C. for 3 hours and then at room temperature for 12 hours. The solution is poured over 260 ml ion-exchange water and a few ice-cubes; crystallization occurs. The material is clarified and dried, to give 46 g of the desired product (Yield: 75.4%).

Purity control:
TLC in eluent benzene/MEK/formic acid 60:25:20
Rf of the amine OH: 0.55
Rf of the O-acetylated amine: 0.75.

(4) Preparation of 2,4,6-tribromo-3-(N-methylacetamido)-5-(N-acetoxyethylcarbamoyl)-pentaacetoxy-gluconyl aniline

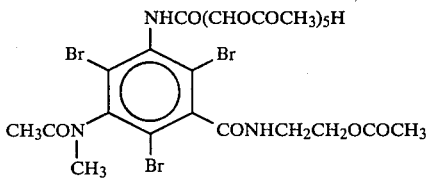

2,4,6-Tribromo-3-N-acetoxyethylcarbamoyl-5-N-methyl-N-acetylamino-aniline (28 g; 0.0573 mole) is suspended in 36 ml dimethylacetamide and pentaacetylated gluconic acid chloride (36.5 g; 0.086 mole) is added portionwise thereto. The reaction mixture is stirred at room temperature for 48 hours. Water (78 ml) is added to the solution which is then stirred for 30 minutes. The aqueous phase is extracted with 4×150 ml dichloroethane. The organic phase is washed with 4×250 ml of a 5% sodium bicarbonate solution, and then with 2×500 ml water.

The material is dried over calcium chloride, filtered and the dichloroethane is evaporated in vacuo, to give 30.5 g of the desired product (Yield: 63%).

Purity control:
TLC in eluent butanol/acetic acid/water 50:11:25
Rf of the amine OH: 0.2
Rf of the O-acetylated amine: 0.65
Rf of the condensed product, prior to saponification: 0.5.

(5) Preparation of 2,4,6-tribromo-3-(N-methylacetamido)-5-(N-hydroxyethylcarbamoyl)-N-gluconyl aniline

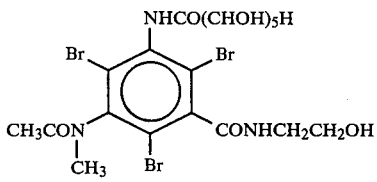

2,4,6-Tribromo-3-(N-methylacetamido)-5-(N-acetoxyethylcarbamoyl)-N-pentaacetoxy-gluconyl aniline (30.5 g; 0.33 mole) is dissolved in a mixture of water (83 ml), hydrazine hydrate (13 ml) and methanol (15 ml). The solution is stirred at 45° C. for 6 hours and then at room temperature for 12 hours. Water (40 ml) and phthalic anhydride (36 g) are added to the mixture which is then stirred at 70° C. for 4 hours and at room temperature for 48 hours.

After suction filtering, the filtration liquids are charcoaled with charcoal 3SA at 60° C. for 3 hours, after which they are evaporated to ⅓ the original volume, and extracted with 6×200 ml ethyl acetate.

The resulting material is evaporated to dryness, to give 13 g of the desired product (Yield: 60%).

Purity control:
TLC in eluent benzene/MEK/formic acid 60:25:10
Rf of the product prior to saponification: 0.05
Rf of the product after saponification: 0.55

EXAMPLES XII and XIII

Using the same procedure as in Examples VII and VIII, the following compounds were obtained:

| Ex. | Formula | | Rf eluent 1⊕ | Rf eluent 2⊕ |
|---|---|---|---|---|
| XII | [structure: 2,4,6-tribromo aniline with COOH, HOCH₂CH₂NHCO, NHCOCH₂NHCO substituents] | [structure: 2,4,6-tribromo aniline with CH₃—N—COCH₂OCH₃, CONHCH₃ substituents] | 0.1 | 0.25 |

| Ex. | Formula | | Rf eluent 1⊕ | Rf eluent 2⊕ |
|---|---|---|---|---|
| XIII | 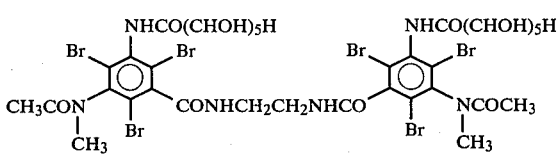 | | 0.05 | 0.2 and 0.25 |

⊕Eluent 1: benzene/methylethylketone/formic acid 60:25:20
⊕Eluent 2: n-butanol/acetic acid/water 50:11:25

EXAMPLE XIV

Preparation of 1,2-N,N'-bis-(2,4,6-tribromo-3-N-methylacetamido-5-N-gluconylamino)diamino-ethane (a) Preparation of 2,4,6-tribromo-3-N-methylacetamido-5-amino-benzoic acid chloride The corresponding acid (20 g) dissolved in SOCl₂ (40 ml) is heated at 80° C. for 2 hours. After evaporation of the thionyl chloride, the oil precipitates in 100 ml isopropyl ether. The resulting material is stirred for 1 hour, suction filtered, washed with ethyl acetate, suction filtered and dried, to give 17 g of the desired compound (Yield: 81.5%).

(b) Preparation of 1,2-N,N'-bis-(2,4,6-tribromo-3-N-methylacetamido-5-amino-benzoyl)-diamino-ethane To the acid chloride (100 g; 0.215 mole) obtained in (a) dissolved in DMAC (190 ml) are added ethylene diamine (10 ml; 0.15 mole) and triethylamine (30 ml). After stirring at room temperature for 4 days, the insoluble is suction filtered, the filtrate is precipitate with 950 ml H₂O, after which it is suction filtered, washed and dried, to give 85.3 g of the desired product (Yield: 44%).

TLC in eluent benzene/MEK/formic acid 50:20:30
Rf acid chloride + ethanolamine 0.70–0.74
Rf of the product obtained 0.90.

(c) Preparation of 1,2-N,N'-bis(2,4,6-tribromo-3-N-methyl-acetamido-5-N-pentaacetoxy-gluconylaminobenzoyl)-diamino-ethane The compound obtained above (0.089 mole) is dissolved in 180 ml DMAC. Pentaacetylated gluconic acid chloride (0,445 mole) is added thereto as a powder which dissolves as it is added.

After stirring for 20 hours at room temperature, the mixture is precipitated with 1.3 liter ice-water. Stirring is maintained overnight. After suction filtering, the crude product is taken up into dichloroethane. The organic phase is washed with 5% NaHCO₃ and with water and then evaporated off. The oil crystallizes from petroleum ether. Yield: 40%

TLC in eluent benzene/MEK/formic acid 60:25:20
Rf 0.38 (starting material Rf 0.46)

(d) Deprotection

Deprotection is effected with sodium methoxide/methanol.

TLC butanol/H₂O/acetic acid (50:25:20) Rf 0.34–0.40

EXAMPLE XV

Preparation of 2,4,6-tribromo-1,3,5-benzene tricarboxylic acid and derivatives thereof (a) Preparation of 2,4,6-tribromo-5-cyanoisophthalic acid 2,4,6-Tribromo-5-amino-isophthalic acid (232 g; 0.555 mole) is dissolved in concentrated sulfuric acid (500 ml) and the solution is then cooled by means of an ice-bath to a temperature between 0° and 5° C. Sodium nitrite (77 g; 1.11 mole) is then added portionwise over 1 hour while maintaining the temperature at 0°–5° C., and the mixture is stirred for a further 2 hours at that temperature. The mixture is then slowly poured over ice, with stirring, and the excess sodium nitrite is destroyed with a sufficient amount of urea solution. While still maintaining the temperature at 0°–5° C., the suspension is neutralized at pH 6 by addition of 5N sodium hydroxide. The mixture is then added to a solution of cuprous chloride (69 g; 0.694 mole) and sodium cyanide (89 g; 1.82 mole) in 1 liter water, and the solution is stirred overnight at room temperature. The pH of the solution is adjusted to 3 by addition of hydrochloric acid, the copper salt precipitate is suction filtered, and the pH is adjusted to 1 with hydrochloric acid. The solution is cooled in an ice-bath and stirring is maintained for a further 16 hours. The resulting precipitate is suction filtered; it is then taken up into 400 ml water, with stirring, plus a sufficient amount of sodium hydroxide for dissolution and neutral pH. The solution is decolorized by stirring for 1 hour with charcoal 3 SA, after which the charcoal is filtered off, and the material is precipitated with dilute hydrochloric acid to give, after suction filtering and washing with a small amount of water, 130 g of white product (Yield: 55%).

Recrystallization from 400 ml methanol gives 77.5 g purified product. Melting point in excess of 300° C.

(b) Preparation of 2,4,6-tribromo-5-carbamoylisophthalic acid

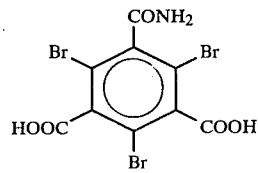

2,4,6-Tribromo-5-cyano-isophthalic acid (60 g; 0.140 mole) is dissolved in 5N sodium hydroxide (120 ml; 0.06 mole). The solution is then stirred at 50° C. for 3 hours, and concentrated hydrochloric acid (50 cc) is then added thereto at room temperature. The reaction mixture is cooled in an ice-bath and stirred for 2 hours. The resulting precipitate is suction filtered, washed with a small amount of ice-water, and dried, to give 60 g of a white product (Yield: 96%). Melting point in excess of 300° C.

TLC: benzene/MEK/formic acid 60:25:20 Rf 0.3.

(c) Preparation of 2,4,6-tribromo-1,3,5-benzene tricarboxylic acid

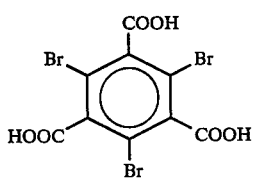

2,4,6-Tribromo-1,3,5-benzene-tricarboxylic acid may be obtained from 2,4,6-tribromo-5-carbamoyl-isophthalic acid by action of a nitrosating agent which may be sodium nitrate in sulfuric acid or hydrochloric acid, an alkylnitrite or nitrosonium tetrafluoroborate in an organic solvent. 2,4,6-Tribromo-5-carbamoyl-isophthalic acid (52.5 g; 0.123 mole) is suspended in a mixture of 700 ml water and 700 ml concentrated hydrochloric acid. The suspension is heated at 90° C. and a solution of sodium nitrite (41 g; 0.595 mole) in 700 ml water is added portionwise thereto, over 7 hours. When addition is complete, stirring is continued for 1 hour, after which the resulting solution is evaporated to dryness, to give 90 g of residue which is taken up into 500 ml ether with stirring for 2 hours. The insoluble sodium chloride is filtered off. The ether phase is evaporated to dryness, to give 49 g of a white powder (Yield: 93%).

Melting point in excess of 300° C.

TLC: benzene/MEK/formic acid 60:25:20 Rf: 0.4.

(d) Preparation of 2,4,6-tribromo-1,3,5-benzene tricarboxylic acid trichloride 2,4,6-Tribromo-1,3,5-benzene-tricarboxylic acid (45 g; 0.1 mole) is suspended in 80 ml (1.1 mole) thionyl chloride. Dimethylformamide (2 ml) is added thereto and the material is refluxed for 2 hours, with stirring. It is then allowed to cool. A white solid crystallizes. This is suction filtered, washed with a small amount of cyclohexane and dried, to give 43 g of product as white needles (Yield: 85%). Melting point: 202° C.

(e) Preparation of 2,4,6-tribromo-1,3,5-tris(2,3-dihydroxypropyl-carbamoyl)benzene 2,4,6-Tribromo-1,3,5-benzene-tricarboxylic acid trichloride (25 g; 0.05 mole) is dissolved in dimethylacetamide (50 cc). A solution of aminopropane-2,3-diol (30 g; 0.33 mole) in dimethylacetamide (60 ml) is then added portionwise thereto. The reaction mixture is then stirred at 50° C. for 3 hours; the pH is adjusted to neutral by addition of hydrochloric acid, and the mixture is evaporated to dryness. The residue is taken up into a minimum amount of water and extracted with phenol. After treatment of the phenol phase with ethyl ether and extraction with water, the aqueous phase is evaporated in vacuo, to give 25 g of a white product (Yield: 76%).

TLC: Benzene/MEK/formic acid 60:25:20 Rf: 0.05
Isobutanol/isopropanol/ammonia 30:30:40
Rf: 0.55–0.60

(f) Preparation of 2,4,6-tribromo-1,3,5-tris(N-methyl-2,3,4,5,6-pentahydroxyhexyl-carbamoyl)benzene The compound is prepared in the same manner as above compound (e).

TLC: Benzene/MEK/formic acid 60:25:20 Rf 0.05
Isobutanol/isopropanol/ammonia 30:30:40 Rf 0.10 and 0.15

(g) Preparation of 2,4,6-tribromo-1,3,5-tris(bishydroxyethyl-carbamoyl)benzene

The compound is prepared in the same manner as above compound (e).

TLC: Benzene/MEK/formic acid 60:25:20 Rf 0.05
Isobutanol/isopropanol/ammonia 30:30:40 Rf: 0.45.

Results of comparative tests effected with mixtures of bromobenzene compounds and iodobenzene compounds are given below.

(1) Opacity

The opacity was determined indirectly by means of the print produced on photographic film by a beam of X-rays passing through a cell containing an aqueous solution of the compounds. The transparency of the film after development was determined with an optical densitometer. In each case, the determination was effected on the same film and with the same X-ray source (70 kV) by comparison with a reference contrast material.

The reference material used, HEXABRIX, is a solution of the sodium and methylglucamine salts of ioxaglic acid containing 32% iodine.

The mixtures were tested as aqueous solutions of mixtures of the methylglucamine salts of the iodo and bromo compounds containing the same total number of moles of compounds as HEXABRIX.

The results obtained are set forth in Table I below.

TABLE I

| Contrast material | Relative opacity/Hexabrix |
|---|---|
| Equimolar mixture of ioxaglic acid methylglucamine salt and of bromo analog (Example VII) | 0.905 |

It is apparent from the above results that the opacity of the mixture is very close to that of HEXABRIX. To obtain with the mixtures the same opacity as that obtained with one mole of solely iodinated product, it is only necessary to use 0.55 mole iodo product and 0.55 mole bromo product.

On the other hand, to take into account the fact that contrast media are diluted in the body, opacity determinations have been effected with different dilutions. It was found that the opacity loss could be very slight. Thus, for a mixture in aqueous solution comprising 40 wt% Telebrix 38 (containing 38% iodine) and 60 wt% bromo analog (compound of Example II-2) the opacity loss with respect to Telebrix 38 varies from 2.5 to 9.5% depending on the dilutions.

For a mixture comprising 50 wt% Contrix and 50 wt% bromo analog (compound of Example I-2) the opacity loss with respect to Contrix varies from 8.1 to 12% depending on the dilutions.

For a mixture comprising 50 wt% Me-Contrix and 50 wt% bromo analog (compound of Example I-3) the opacity loss with respect to Me-Contrix varies from 6 to 7.9%, depending on the dilutions.

(2) Acute intracisternal toxicity

Acute intracisternal toxicity was determined by the method of E. Melartin, P. Tuohimaa, R. Dabb, Investigative Radiology, 1970, vol. 5, n°1, 13–21.

The results obtained are given in Table II below.

TABLE II

| Contrast material | Acute toxicity IC (DL50) | |
|---|---|---|
| | Rats mole/rat | Mice g Eq iodine/kg |
| Contrix (methylglucamine iothalamate) | 0.028 | |
| Equimolar mixture Contrix + bromo analog (methylglucamine salt of the compound of Example I-2) | 0.033 | |
| Telebrix | | 0.2 |
| Equimolar mixture Telebrix + bromo analog (methylglucamine salt of the compound of Example II-2) | | 0.35 |

(3) Protein binding

The degree of the interaction with proteins is an index of the tolerance of contrast media. The lower this interaction, the better the tolerance.

The protein binding was investigated according to the Brodersen technique (J. of Clinical Investigation, 1974, vol. 4, 1353–1364).

The results obtained are given in following Table III.

TABLE III

| Contrast material | Protein binding moles$^{-1}$ |
|---|---|
| Methylglucamine ioxaglate | 122 |
| Equimolar mixture methylglucamine ioxaglate + bromo analog (methylglucamine salt of the compound of Example VII) | 102 |
| Methylglucamine adipiodone | 12800 |
| Equimolar mixture methylglucamine adipiodone + bromo analog (methylglucamine salt of the compound of Example VI) | 8100 |

Therefore, the mixtures of iodo compounds and of bromo compounds may be used as X-ray contrast media.

The preferred pharmaceutical form consists of aqueous solutions of mixtures of iodo and bromo compounds.

The aqueous solutions generally contain 5–100 g of a mixture of iodo compounds and of bromo compounds and the injectable amount of such solutions may generally vary from 5 to 1000 ml.

Examples of compositions according to the present invention are given below.

| Composition A | |
|---|---|
| Methylglucamine iothalamate | 30 g |
| Methylglucamine salt of the compound of Example I-2 | 25 g |
| Water for injectable preparation, sufficient, to make | 100 ml |

| Composition B | |
|---|---|
| Methylglucamine ioxitalamate | 24 g |
| Methylglucamine salt of the compound of Example II-2 | 30 g |
| Water for injectable preparation, sufficient to make | 100 ml |

| Composition C | |
|---|---|
| Methylglucamine ioxaglate | 30 g |
| Sodium salt of the compound of Example I-3 | 25 g |
| Water for injectable preparation sufficient to make | 100 ml |

| Composition D | |
|---|---|
| Methylglucamine ioxaglate | 25 g |
| Methylglucamine salt of the compound of Example VII | 30 g |
| Water for injectable preparation sufficient to make | 100 ml |

| Composition E | |
|---|---|
| Methylglucamine ioxaglate | 30 g |
| Methylglucamine salt of the compound of Example I-2 | 25 g |
| Water for injectable preparation sufficient to make | 100 ml |

We claim:

1. X-ray contrast media, for which the human body has a greater tolerance than that of contrast media comprising solely iodobenzene compounds, and an opacity of the same order of magnitude as said contrast media, comprising mixtures of benzene compounds nuclearly substituted with a plurality of iodine atoms and of benzene compounds nuclearly substituted with a plurality of bromine atoms, wherein the bromobenzene compounds represent from ½ to 2/1 (in moles) of the iodobenzene compounds.

2. X-ray contrast media as claimed in claim 1, which contain mixtures of two or more of the following compounds, at least one of which is a bromo compound and at least another of which is an iodo compound:

I—Compounds of the formula:

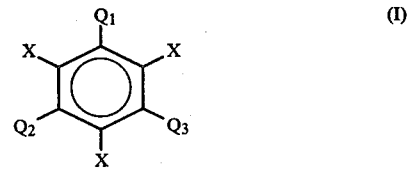

(I)

in which:
the substituents X are selected from I and Br, and $Q_1$, $Q_2$ and $Q_3$ are pharmacologically acceptable groups, II—Compounds of the formula:

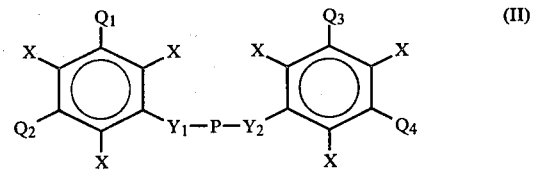

(II)

in which:
the substituents X are selected from I and Br, and $Q_1$, $Q_2$, $Q_3$, $Q_4$, $Y_1$, $Y_2$ and P are pharmacologically acceptable groups, III—Compounds of the formula:

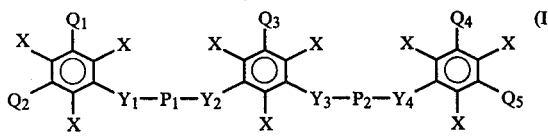 (III)

in which:
the substituents X are selected from I and Br, and
$Q_1$, $Q_2$, $Q_3$, $Q_4$, $Q_5$, $Y_1$, $Y_2$, $Y_3$, $Y_4$, $P_1$ and $P_2$ are pharmacologically acceptable groups, IV—Compounds of the formula:

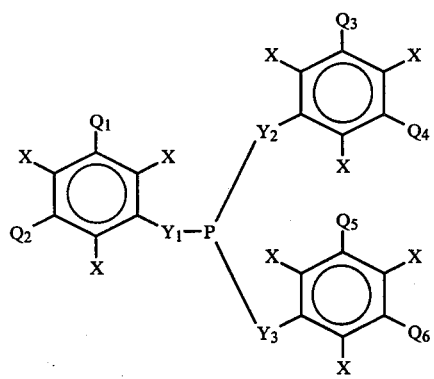 (IV)

in which:
the substituents X are selected from I and Br, and
$Q_1$, $Q_2$, $Q_3$, $Q_4$, $Q_5$, $Q_6$, $Y_1$, $Y_2$, $Y_3$ and P are pharmacologically acceptable groups.

3. X-ray contrast media as claimed in claim 1, which contain mixtures of two or more of the following compounds, at least one of which is a bromo compound and at least another of which is a iodo compound:

1—compounds of the formula:

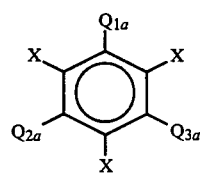 (Ia)

in which:
X is selected from Br and I
$Q_{1a}$ is a —COOH group or a salt thereof with a pharmacologically acceptable base
$Q_{2a}$ is selected from a hydrogen atom; a radical of the formula

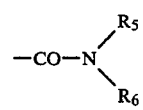

in which $R_5$ and $R_6$ are independently from one another selected from a hydrogen atom, a lower alkyl radical, a lower hydroxyalkyl radical, and a lower alkanoyloxy lower alkyl radical; an amino group; and a radical of the formula

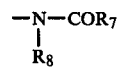

in which $R_7$ is selected from a lower alkyl radical, a lower hydroxyalkyl radical, and a lower alkoxy lower alkyl radical, and $R_8$ is selected from a hydrogen atom, a lower alkyl radical and a lower hydroxyalkyl radical;

$Q_{3a}$ is selected from an amino group and a radical of the formula

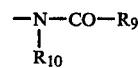

in which $R_9$ and $R_{10}$ have the meanings given for $R_7$ and $R_8$, respectively;

2—compounds of the formula:

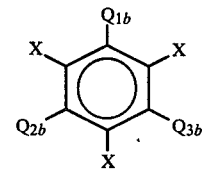 (Ib)

in which:
X is selected from Br and I,
$Q_{1b}$ represents a radical of the formula

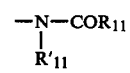

in which $R_{11}$ is a polyhydroxy lower alkyl radical and $R'_{11}$ is selected from a hydrogen atom and a lower alkyl radical, $Q_{2b}$ represents a radical of the formula

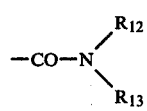

in which $R_{12}$ and $R_{13}$ have the meanings given for $R_5$ and $R_6$, respectively, $Q_{3b}$ is selected from a radical of the formula

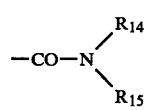

in which $R_{14}$ and $R_{15}$ have the meanings given for $R_5$ and $R_6$, respectively, and a radical of the formula

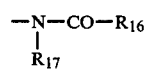

in which $R_{16}$ and $R_{17}$ have the meanings given for $R_7$ and $R_8$, respectively;

3—compounds of the formula:

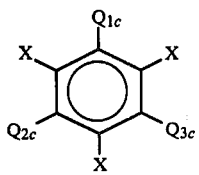
(Ic)

in which:
X is selected from Br and I,
$Q_{1c}$ represents a radical of the formula —CONH—$R_{18}$ in which $R_{18}$ is selected from a sugar residue and a polyhydroxy lower alkyl radical,
$Q_{2c}$ represents a radical of the formula

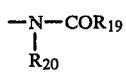

in which $R_{19}$ and $R_{20}$ have the meanings given for $R_7$ and $R_8$, respectively, and is selected from a radical of the formula

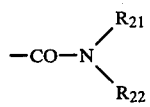

in which $R_{21}$ and $R_{22}$ have the meanings given for $R_5$ and $R_6$, respectively, and a radical of the formula

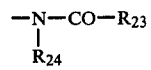

in which $R_{23}$ and $R_{24}$ have the meanings given for $R_7$ and $R_8$, respectively;
4—compounds of the formula:

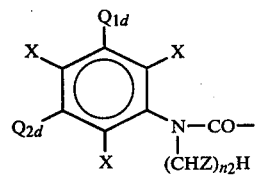
(IIa)

in which:
X is selected from Br and I,
$Q_{1d}$ is a —COOH group or a salt thereof with a pharmacologically acceptable base,
$Q_{2d}$ and $Q_{3d}$ are radicals which have the same meanings as $Q_{2a}$, and $Q_{2d}$ may also represent a radical —CH$_2$OH,
$Q_{4d}$ is selected from a group —NH$_2$ and a radical of the formula

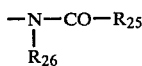

in which $R_{25}$ has the meaning given for $R_7$ and $R_{26}$ is selected from the radicals given for $R_8$ and a lower alkanoyl radical,
Z is selected from H and OH
$n_1$ is an integer from 1 to 5,
$n_2$ is an integer from 0 to 6;
5—compounds of the formula:

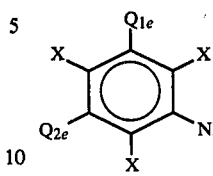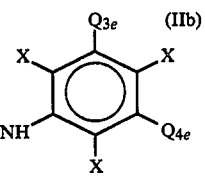
(IIb)

in which:
X is selected from Br and I,
$Q_{1e}$ and $Q_{3e}$ are —COOH groups or salts thereof with pharmacologically acceptable bases
$Q_{2e}$ and $Q_{4e}$ have the meanings given for $Q_{2a}$;
6—compounds of the formula:

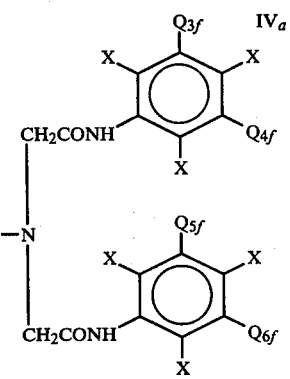
IV$_a$ in which:
X is selected from Br and I,
$Q_{1f}$ is a —COOH group or a salt thereof with a pharmacologically acceptable base,
$Q_{2f}$, $Q_{3f}$, $Q_{4f}$, $Q_{5f}$ and $Q_{6f}$ have the meanings given for $Q_{2a}$,
Z is selected from H and OH, and
n is an integer from 0 to 6;
7—compounds of the formula:

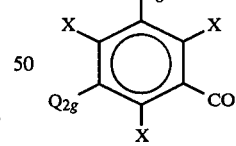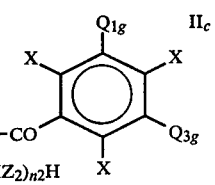
II$_c$ in which:
X is selected from Br and I,
$Q_{1g}$ represents a radical of the formula

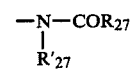

in which $R_{27}$ is a polyhydroxy lower alkyl radical and $R'_{27}$ is selected from a hydrogen atom and a lower alkyl radical,
$Q_{2g}$ and $Q_{3g}$ represent independently from one another a radical selected from a radical

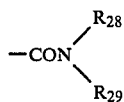

in which $R_{28}$ and $R_{29}$ are independently selected from a hydrogen atom, a lower alkyl radical, a lower hydroxyalkyl radical, and a lower alkanoyloxy lower alkyl radical; an amino group; and a radical of the formula

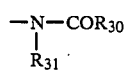

in which $R_{30}$ is selected from a lower alkyl radical, a lower hydroxyalkyl radical and a lower alkoxy lower alkyl radical, and $R_{31}$ is selected from a hydrogen atom, a lower alkyl radical and a lower hydroxyalkyl radical, $Z_1$ and $Z_2$ are independently from one another selected from H and OH, $n_1$ and $n_2$ represent independently from one another an integer from 0 to 6, and $n_3$ represents an integer from 0 to 4;

8—compounds of the formula:

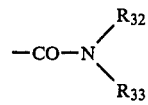

in which:

X is selected from Br and I, $Q_{1h}$, $Q_{2h}$ and $Q_{3h}$ are independently from one another selected from a —COOH group, a —COOH group converted to a salt with a pharmacologically acceptable base, and a group of the formula $$-CO-N\begin{matrix}R_{32}\\R_{33}\end{matrix}$$

in which $R_{32}$ and $R_{33}$ represent independently from one another a radical selected from a hydrogen atom, a lower alkyl radical, a lower hydroxyalkyl radical, and a lower alkanoyloxy lower alkyl radical.

4. X-ray contrast media as claimed in claim 3, which consist essentially of an aqueous solution of a mixture of iodobenzene compounds and of bromobenzene compounds.

* * * * *